Figure 1:
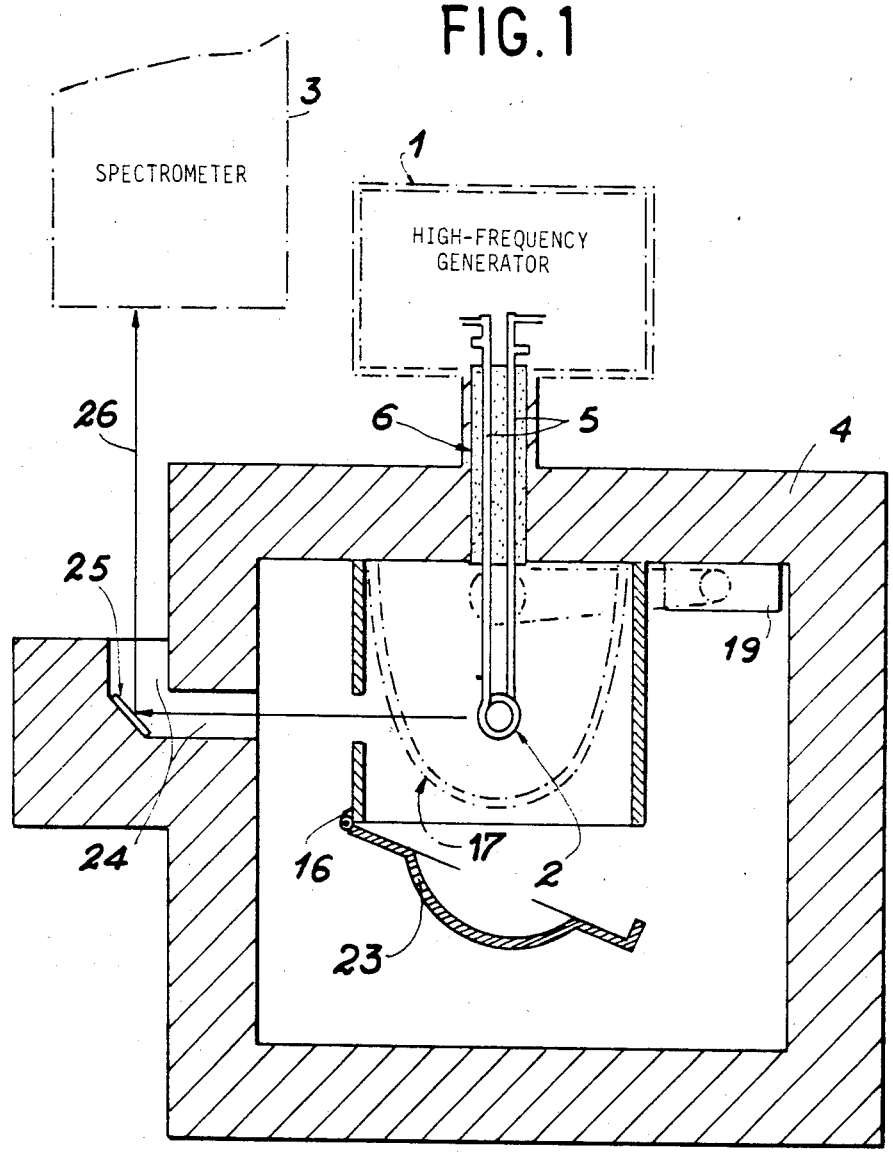

United States Patent [19]

Andrieu et al.

[11] Patent Number: 4,664,477

[45] Date of Patent: May 12, 1987

[54] SHIELDED AIR-TIGHT ENCLOSURE EQUIPPED FOR USE IN EMISSION SPECTROMETRY

[75] Inventors: Guy Andrieu, Bagnols sur Ceze; Jean-Marc Blanchard, Remoulins; Michel Sourrouille, Laudun, all of France

[73] Assignee: Compagnie Generale des Matieres Nucleaires (Cogema), Velizy Villacoublay, France

[21] Appl. No.: 733,954

[22] Filed: May 14, 1985

[30] Foreign Application Priority Data

May 14, 1984 [FR] France .................. 84 07411

[51] Int. Cl.⁴ ........................................... G01N 21/73
[52] U.S. Cl. .................................. 356/316; 250/515.1
[58] Field of Search ............... 356/311, 315, 316, 417; 250/515.1

[56] References Cited

U.S. PATENT DOCUMENTS 4,300,834 11/1981 Demers et al. ...................... 356/316

FOREIGN PATENT DOCUMENTS 1462304 12/1966 France .
0098447 7/1980 Japan ................. 250/515.1
0094042 5/1984 Japan ................. 356/316

OTHER PUBLICATIONS

Crider, *Analytical Chemistry*, vol. 37, No. 13, Dec. 1965, pp. 1770–1773.

*Primary Examiner*—F. L. Evans

[57] ABSTRACT

The invention relates to an air-tight, shielded enclosure equipped for emission spectrometry. The air-tight enclosure (4) outside of which the high-frequency generator (1) and the spectrometer (3) are located, contains the inductor plasma source (2). The enclosure is provided with an insulating and biologically protective high-frequency lead-through (6), a Faraday cage (16), an air removing hood (17), and a baffle output (24) of the image of the plasma. This equipment makes it possible to apply emission spectrometry to the analysis of radioactive elements.

1 Claim, 3 Drawing Figures

SHIELDED AIR-TIGHT ENCLOSURE EQUIPPED FOR USE IN EMISSION SPECTROMETRY

BACKGROUND OF THE INVENTION

The subject matter of the present invention is a shielded, air-tight enclosure equipped so as to be usable in emission spectrometry.

The emission spectrometry method of analysis, with its traditional arc-spark sources, has been known for several decades.

At the present time a new source, called an "inductive coupling plasma" (ICP) is being used in many laboratories.

In these known apparatus a high-frequency power source supplies electrical energy to a hollow cylindrical inductor made by winding successive turns of hollow copper tubing inside of which cooling water circulates.

The solution containing the chemical elements to be analyzed is vehicled in the form of a fog by a current of inert gas, such as argon, circulating axially within the coil of the inductor, such that the powers, raised to a sufficient frequency, dissipated by this inductor create in an axial zone of this inductor a high-temperature plasma.

A spectrometer, centered on this plasma, makes it possible to determine and quantify the different cations present in the solution by studying the emission spectrum.

This method permits the analysis of the cations within detection limits close to a microgram per liter, allowing very great dilutions of the elements to be analyzed in the solution.

Furthermore, this method of analysis involves but a very small consumption of the solution, of the order of 5 milliliters per hour, when the fog is produced by ultrasound.

Another advantage of this method is the speed of the analysis, which is performed in about one minute per element metered.

Lastly, the precision obtained, of the order of 1%, is decidedly improved in comparison with other usable arc or spark sources of plasma.

These advantages of this method of analysis are of very particular interest for reasons of nuclear safety, when it is desired to analyze radioactive elements of fission products, because naught but extremely small quantities of these elements are used.

Nevertheless, it is necessary to perform the analysis in a shielded, air-tight enclosure.

The present invention is more precisely related to the equipment of an air-tight enclosure permitting the application of the emission spectrometry analysis method set forth above, to radioactive chemical elements in solution.

As it is well known in nuclear technology, when an apparatus that is to be operated in a shielded enclosure is designed, the effort is made to put only a minimum of parts, devices or equipment of the apparatus within this enclosure, and to construct these different components so that they will be as simple as possible so as to be easily handled by means of telemanipulators, and so that their reliability and useful life will be as great as possible.

In the case of the emission spectrometry apparatus concerned by the invention, the general thrust of the design of the apparatus was therefore to house within the shielded enclosure only the active part in contact with radioactive elements, that is to say, the inductively coupled plasma source, and to locate outside of the shielded enclosure the high-frequency generator, on the one hand, and the spectrometer on the other.

To do this it was necessary first of all to remove this plasma source physically away from the high-frequency generator by a distance of several tens of centimeters and to connect them through the shielded wall of the enclosure.

This first problem was solved by a first invention of the same inventors, which is the subject matter of French Patent Publication No. 2564233 entitled, "Improved inductor for a plasma source, usable in emission spectrometry."

This inductor is characterized in that it includes two powersupply conductors of a length between 20 and 40 cm, constituted by two hollow, stainless steel tubes connected at one of their ends to coils made of a hollow, stainless steel tube, their other ends to be connected electrically to a high-frequency generator, and means being provided for circulating cooling air within the said connected hollow tubes.

It is the purpose of the present invention to provide an apparatus for the equipment of an air-tight enclosure adapted to this type of inductors and to the general configuration of emission spectrometry apparatus, mentioned above.

THE INVENTION

To this effect, the present invention concerns a shielded, air-tight enclosure equipped to be usable in emission spectrometry, characterized in that it includes, in association:

a lead-through device for a wall of the shielded enclosure, to accommodate high-frequency power supply tubes for a plasma source inductor, including means of electrical insulation of the tubes from one another and from the metal parts of the wall, and of biological protection, a Faraday cage within which the said inductor is placed and grounded with the metal parts of the wall, an air aspiration hood placed above the inductor and including means for cooling this air, and a baffled aperture in the shielded wall, equipped with a mirror to permit the optical output of an image of the plasma with biological safeguards.

An embodiment of the invention will now be described by way of example.

Figure 2:
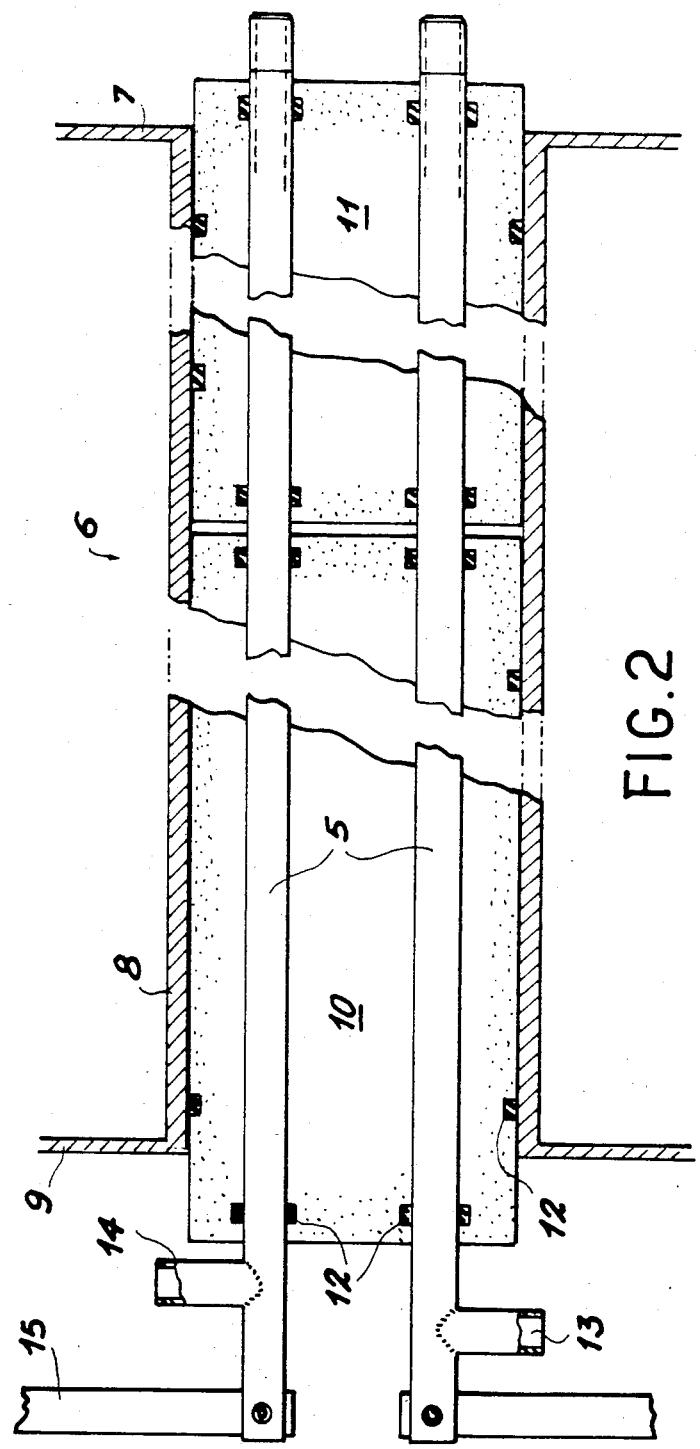
Figure 3:
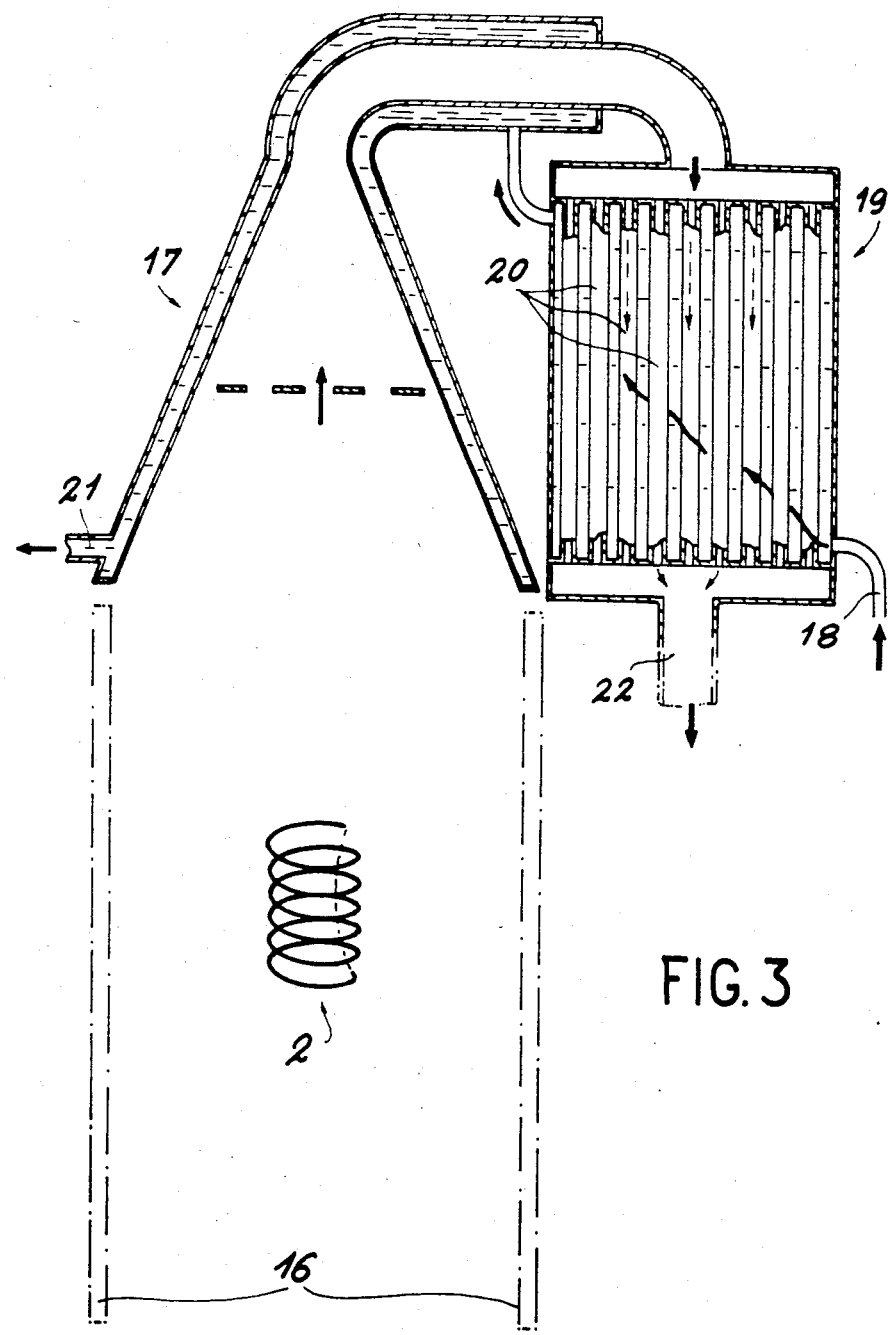

Referring to the appended drawing:

FIG. 1 represents a diagrammatic top view of an emission spectrometry apparatus the active part of which is located within a shielded enclosure equipped in accordance with the invention, FIG. 2 is a view partially in horizontal cross section showing in greater detail the device for leading through the shielded wall, and FIG. 3 is a fragmentary view in vertical cross section showing in greater detail the Faraday cage as well as the air aspirating hood and its cooling means.

As set forth above, the emission spectrometry apparatus includes essentially a high-frequency generator, indicated at 1, supplying electrical energy to the inductor 2 of a plasma source and the emission spectrum of this plasma is analyzed by a spectrometer indicated at 3.

To apply the emission spectrometry analysis method to radioactive elements contained within a shielded, air-tight enclosure 4, all that has been located within the enclosure 4 is the inductor 2 constituting the active part of the plasma source, while the high-frequency generator 1 and the spectrometer 3 have been kept outside.

For this purpose, according to one of the first provisions of the invention, the inductor 2 has been removed physically several tens of centimeters away from the high-frequency generator 1, which becomes possible with an inductor of the kind covered by the above-mentioned French Patent Publication 2564233 which gives a complete and detailed description of this new type of inductor. It will suffice here to mention that this inductor is electrically powered through two hollow, stainless steel, air-cooled tubes 5 of a length of 20 to 40 cm, sufficient to separate the generator 1 from the inductor 2 and enable the tubes to pass through the shielded wall of the air-tight enclosure 4 by a lead-through device 6.

FIG. 2 represents this lead-through device in greater detail. The outer rear metal wall 7 of the shielded enclosure 4 is connected by a cylindrical metal sleeve 8 to the vertical rear wall 9 of the high-frequency generator 1. The two feeder tubes 5 of the inductor are insulated within two successive blocks 10 and 11 made, for example, of plastic material such as the plastic material known by the commercial name "teflon." Seals 12 made, for example, of plastic material such as the plastic material known by the commercial name "viton" complete the electrical and nuclear sealing of this lead-through device.

Cooling air is introduced into one of the tubes 5 through an inlet 13, circulates inside of the tubes 5 and the coils of the inductor 2, and leaves through an outlet 14 formed in the other tube. The tubes 5 are electrically connected to the high-frequency receiving frame 15 of the generator.

The two blocks 10 and 11 constitute a push-push device known in itself, permitting the partial or complete replacement of the safeguard without loss of alpha radiation protection and with a minimal gamma radiation protection which is what is then provided by only one of the two blocks 10 and 11, this being done from the exterior of the enclosure. Likewise, this construction of the lead-through device makes it possible from the outside of the enclosure to disconnect the tubes 5 from those forming the coil of the inductor 2 when it is necessary or useful to replace or change this inductor.

The shielded enclosure 4 is equipped, according to a second provision of the invention, with a Faraday cage having two confronting vertical plates 16 placed one on each side of the inductor 2, as shown in FIGS. 1 and 3. The two plates 16 are connected to one another by a hinged plate 23 serving as a door. The purpose of this Faraday cage is to prevent the high-frequency radiation of the inductor from affecting the rest of the air-tight enclosure 4. This Faraday cage is grounded by means of electrical leads between the cage and the metal parts of the shielded enclosure.

According to a third provision of the invention, the shielded enclosure 4 is equipped with an air intake hood 17 (FIGS. 1 and 3) placed above the inductor 2. This hood, together with the plates 16, completes the above-mentioned Faraday cage. The hood, of truncoconical shape, is double-walled. Cooling water is introduced through an inlet pipe 18 into a heat exchanger 19 where it circulates around tubes 20. Upon leaving the exchanger 19, the water circulates between the two walls of the hood to cool it, before exiting through an outlet passage 21. Air, aspirated through the hood, is introduced into this heat exchanger to be cooled by circulating inside of the tubes 20. It is then removed through a passage 22.

According to a fourth provision of the invention (FIG. 1), a baffle outlet 24 equipped with a mirror 25 is provided through one shielded wall of the air-tight enclosure 4 to make it possible to form from the plasma situated inside of the inductor coil 2 an optical image aimed at the spectrometer 3, as indicated by the optical path 25.

The invention can obviously assume other concrete forms than the embodiment described above in a manner which is deliberately schematic yet very precise from the operational point of view.

We claim:
1. An air-tight enclosure assembly for performing emission spectrometry analysis of radioactive chemical elements in solution, said assembly comprising:
   an air-tight enclosure having a wall comprising metal parts;
   a plasma source inductor located within the enclosure;
   a high frequency generator located outside the enclosure;
   a lead-through device traversing said wall, said lead-through device comprising tubes interconnecting said high-frequency generator and said plasma source inductor, and biological protection means electrically insulating the tubes from one another and from said metal parts of the wall;
   a Faraday cage located within the enclosure and within which said inductor is placed, said Faraday cage being grounded by connection to said metal parts of the wall;
   an air aspiration hood located within the enclosure, around the inductor, said hood being provided with means for cooling the air; and
   a baffle outlet provided in said wall and having a mirror operable to transmit an optical image of the plasma in the enclosure to the spectrometer outside the enclosure.

* * * * *